United States Patent [19]
Griffith et al.

[11] Patent Number: 5,093,478
[45] Date of Patent: Mar. 3, 1992

[54] PREPARING GLUTATHIONE MONOESTERS

[75] Inventors: Owen W. Griffith, New York; Ernest B. Campbell, Corona, both of N.Y.

[73] Assignee: Cornell Research Foundation, Inc., Ithaca, N.Y.

[21] Appl. No.: 379,771

[22] Filed: Jul. 14, 1989

[51] Int. Cl.$^5$ ............................................. A61K 37/02
[52] U.S. Cl. .................... 530/331; 530/345; 560/40; 560/41
[58] Field of Search ............... 530/331, 345; 514/18; 560/40, 41

[56] References Cited

U.S. PATENT DOCUMENTS

| | | | |
|---|---|---|---|
| 3,482,025 | 12/1969 | Murakami | 514/419 |
| 3,741,948 | 6/1973 | Murakami | 530/337 |
| 4,390,619 | 6/1983 | Harmening-Pittiglio | 435/2 |
| 4,709,013 | 11/1987 | Nagano | 530/332 |
| 4,710,489 | 12/1987 | Meister | 514/18 |
| 4,784,685 | 11/1988 | Meister | 71/106 |
| 4,924,027 | 5/1990 | Kulprathipanja et al. | 562/580 |

FOREIGN PATENT DOCUMENTS 249401 12/1987 European Pat. Off. .
257992 3/1988 European Pat. Off. .

OTHER PUBLICATIONS

Morrison & Boyd 3rd Ed. *Organic Chemistry* (Allyn & Bacon 1973) 602–603.
Freifelder, 2nd Ed. *Physical Biochemistry* (Freeman & Co. 1982) at 248–257.
Wharton & McCarty, *Experiments and Methods in Biochemistry* (Macmillan Co. 1972) at 101–105.
Diaion Data Sheet High Porous Polymer HP Series, Mitsubishi Chemical Industries, Ltd, 3/85.

*Primary Examiner*—Lester L. Lee
*Assistant Examiner*—B. Celsa

[57] ABSTRACT

In the esterification of glutathione with alcohol in the presence of acid catalyst, neutral glutathione monoester is isolated in high yields without the intermedite isolation of ester acid salt by treating the reaction mixture with base anion exchange resin (basic form) to neutralize the acid and bind the resulting acid anion and unesterified glutatione. Dehydrating agent is used to drive the reaction toward esterification. In the production of glutathione monester acid salts a soluble dehydrating agent is advantageously used.

7 Claims, No Drawings

PREPARING GLUTATHIONE MONOESTERS

This invention was made at least in part with Government support under National Institutes of Health grant number DK 26912. The Government has certain rights in the invention.

TECHNICAL FIELD

This invention is directed to preparing neutral glutathione monoesters.

BACKGROUND OF THE INVENTION

Glutathione is a known constituent of mammalian cells. Increased levels thereof are known to diminish the cytotoxic effects of radiation, cadmium, acetominophen, and anticancer drugs such as BCNU (i.e., 1,3-bis(2-chloroethyl)-1-nitosourea) and cyclophosphamide. Since glutathione itself does not effectively cross cell membranes, alternative strategies of increasing intracellular levels of glutathione have been developed. The most effective and generally useful of these is administering glutathione monoesters. Conventionally these monoesters are prepared by reacting glutathione with an alcohol in the presence of an acid and have been, in all cases, initially isolated as acid salts. Administration parenterally to mammals of acid salts requires coadministration of neutralizing agent. Such neutralizing agent increases the osmolarity and ionic strength of the adminstered solution, and in typical pharmacological quantities such increases may significantly disturb system balances. Therefore, the isolated acid salts are typically converted to the neutral esters prior to administration. Despite the inconvenience of and decreased yield attendant to isolating first the salt and then the neutral ester, a procedure for preparing neutral esters without first isolating the acid salts has not heretofore been disclosed.

SUMMARY OF THE INVENTION

The invention herein involves forming neutral glutathione mono $C_{1-10}$ alkyl ester in which the glycine carboxyl is esterified by a method comprising reacting glutathione with $C_{1-10}$ saturated alcohol in the presence of strong acid catalyst to form and isolate said ester without the intermediate isolation of the ester acid salt.

This method preferably comprises the steps of (a) esterifying glutathione with $C_{1-10}$ saturated alcohol in the presence of strong acid catalyst under conditions such that glutathione and its esters remain soluble, (b) treating the product of step (a) with base ion exchange resin (basic form) to neutralize the acid to bind the acid anion and to bind unesterified glutathione, (c) separating the resulting resin and associated bound materials to leave a neutral clear solution, (d) crystallizing said neutral monoester from said neutral clear solution.

DETAILED DESCRIPTION

The alkyl of the ester group of said glutathione mono $C_{1-10}$ alkylester can be linear or branched and can be, for example, methyl, ethyl, n-propyl, isopropyl, n-butyl, isobutyl, s-butyl, t-butyl, n-hexyl, heptyl, octyl, nonyl or decyl. Preferably said alkyl is methyl, ethyl or isopropyl.

We turn now to step (a) described above.

Glutathione is readily commercially available and inexpensive.

The $C_{1-10}$ saturated alcohols are linear or branched, primary, secondary or tertiary, monohydric alcohols, such as methanol, ethanol, isopropanol, isobutanol, s-butanol, t-butanol, pentanol, hexanol, heptanol, octanol, nonanol, and decanol. Methanol, ethanol and isopropanol are preferred.

The strong acid catalyst can be any strong acid which does not degrade the base anion exchange resin of step (b) and does not oxidize the sulfhydryl group of glutathione or otherwise degrade glutathione and can be, for example, a mineral or organic acid. Suitable mineral acids include, for example, sulfuric acid and hydrochloric acid. Suitable organic acids include, for example, para-toluenesulfonic acid. Sulfuric acid or other acids which when neutralized in step (b) yields an anion which binds tightly to the base anion exchange resin is preferred. Sulfuric acid when used should be at least 96% $H_2SO_4$ by acidometry. Fuming sulfuric can be used but when it is, it is preferably added after prior dilution with, for example, 2 to 5 volumes of inert solvent such as ethyl ether, to prevent local overheating and resulting discoloration.

The alcohol reactant, for purposes of esterification, needs to be used in at least a stoichiometric amount. In the absence of cosolvents (i.e., where the alcohol also is relied on to provide a solvent function), the alcohol should be used in quantities sufficient to maintain the solubility of glutathione and its esters. Preferably, sufficient alcohol is utilized to minimize the risk of premature crystallization of glutathione monoester before removal of the resin in step (c). Preferably, the amount of alcohol should not be so large as to prevent crystallization in at least 70% yield of neutral monoester in step (d) without reduction of the solution volume. Bearing in mind all of the above, in the absence of cosolvent, ethanol and isopropanol are preferably used in an alcohol to glutathione volume/weight ratio (ml/gm) ranging from 35:1 to 50:1.

The strong acid catalyst is used in a catalytically effective amount, normally 2 to 4 molar equivalents in comparison to the molar amount of glutathione.

The reaction temperature in step (a) normally ranges, for example, from 0° C. to 50° C., preferably, from 20° C. to 30° C.

The reaction time should be sufficient to reduce unreacted glutathione to less than 10%, preferably less than 3%, of original. As soon as unreacted glutathione has been reduced below 3% of original, reaction should preferably be terminated by beginning step (b); termination of the reaction at this point assures minimal formation of diester, typically less than 5%. For ethanol and isopropanol reactants, reaction times generally range from 1 to 48 hours and in the preferred temperature range of 20° C. to 30° C. the reaction time preferably ranges from 4 to 6 hours for ethanol and 40 to 60 hours for isopropanol.

Progress of the esterification is readily monitored by high performance liquid chromatography (HPLC) or, less quantitatively, by thin layer chromatography (TLC) on small silica plates using as solvent n-propanol:acetic acid:water (10:1:5, V/V/V). For suitable HPLC conditions, see Newton, G. L., et al, Anal. Biochem, 114, 383–387 (1981). For suitable TLC conditions, see Anderson, M. E., et al, Arch, Biochem. Biophys. 239, 538–548 (1985).

The conditions related to maintaining the solubility of glutathione and formed esters are the amount of alcohol, the amount of catalyst and the reaction temperature. Use of too little alcohol or catalyst or too low a temperature can result in premature precipitation or crystallization of reactant or products.

In the reaction of step (a) the alcohol is reacted with glycine carboxyl of glutathione to form ester of said carboxyl and water.

The reaction of step (a) preferably is carried out in the presence of dehydrating agent to remove water product of esterification to drive the esterification reaction in the direction of ester formation. Preferably, said dehydrating agent should be alcohol insoluble so that it is removed concomitantly with resin in step (c) and water soluble so as to be easily dissolved and removed during regeneration of the resin with aqueous solutions. Preferably, the dehydrating agent is sodium sulfate or magnesium sulfate, used in a dehydrating effective amount, e.g., a 3 to 5 fold weight ratio to glutathione.

We turn now to step (b).

The base ion exchange resin in step (b) is used in the basic form, e.g., the hydroxide or bicarbonate forms of quaternary resins or the free base form of non-quaternary base resins. A preferred resin in Dowex 1, which is available from Bio-Rad (located in Richmond, Calif.) and is a strong base anion exchange resin. Such resins, if procured in a non-basic form, e.g., chloride form, are readily converted to basic form, e.g., hydroxide or bicarbonate form, by methods well known in the ion exchange resin art.

Said resin is generally used in a stoichiometric excess up to about 25% over the amount needed to neutralize and bind the catalyst. Sufficient excess should be present to also bind unesterified glutathione. In practice the amount of resin added is the minimum required to give a neutral supernatant (i.e., liquid free of solids) free of sulfate. The presence of sulfate is readily detected as insoluble barium sulfate on addition of supernatant sample to aqueous barium chloride.

During step (b) the temperature should be such that glutathione monoester does not precipitate or crystallize prematurely (i.e., before step (d)) and should be low enough to minimize decomposition or hydrolysis of the monoester product. For ethyl and isopropyl monoester products, the preferred temperature in step (b) ranges from about 25° C. to about 30° C.

Preferably, the resin is added to the product of step (a) with continuous mixing to keep the resin suspended. Reaction of the acid catalyst with the base anion resin occurs rapidly over a period of 3 to 10 minutes.

Alternatively, the product of step (a) is allowed to flow through a column containing sufficient base anion exchange resin to neutralize the solution, bind soluble sulfate and glutathione and not bind a significant percentage of product monoester.

The separation of step (c) is readily carried out by conventional solids liquids separation methods, e.g., filtering or centrifuging. Crystallization begins almost immediately from the resulting clear solution.

We turn now to step (d). This is preferably carried out by chilling the neutral clear solution separated in (c) to a temperature ranging, for example, from 20° C. to −20° C. and maintaining said temperature until crystallization is substantially complete. The yield improves with lower temperature limited only by the freezing point of the solution. Temperatures up to room temperature and above can be used but this reduces yield.

Crystals forming in step (d) are essentially pure neutral monoester. The diester stays in solution. The crystals formed in step (d) are readily isolated by conventional solids liquids separation techniques, preferably by filtration. The yield of monoester is 65–75% providing the appropriate amount of alcohol was used in step (a). Correction for too much alcohol in step (a) is readily obtained by removing some solvent by evaporation at reduced pressure before chilling in step (d).

It is preferred to regenerate the used resin separated in step (c) by methods well known in the art. For example, used Dowex 1 resin is regenerated to the hydroxide form by washing with 2N sodium hydroxide, water, and absolute alcohol, in that order; this procedure also solubilizes and removes dehydrating agent such as sodium sulfate or magnesium sulfate.

The use of dehydrating agent to drive the esterification reaction is not only useful in the process described above but also in the case where acid salt is isolated at the conclusion of step (a). Since insoluble dehydrating agents such as sodium sulfate must be removed prior to isolating acid salt, it is desirable when acid salt is to be the isolated product, to use a soluble dehydrating agent, e.g., 2,2-dialkoxypropane which reacts with water to form acetone and two equivalents of alcohol which becomes part of the alcohol solvent.

Inventive embodiments are illustrated in the following specific examples.

EXAMPLE I

Absolute ethanol (200 ml) and a magnetic stirring bar are placed in a 1 L round bottom flask, and the flask is fitted with a stopper. Sulfuric acid, reagent grade, 96.6% $H_2SO_4$ (3 ml, about 54 mmol) is added dropwise to the stirring ethanol. Glutathione (5.0 gm, 16.5 mmol) is suspended in the acidic ethanol solution, and stirring is continued about 15 min. until a clear solution results. Anhydrous sodium sulfate (20 gm) is then added to the solution, and the mixture is stirred 4 to 6 hr. at 25° to 30° C. Process of the esterification is monitored by high performance liquid chromatography by the method of Newton referenced above. The esterification is allowed to continue until remaining glutathione constitutes <3% of the products present.

To isolate the monoester, dry Dowex 1 resin (obtained from Bio-Rad in the chloride form and converted to the hydroxide form and dehydrated by washing with 2N sodium hydroxide, water and absolute ethanol, in that order; 200–400 mesh; nominally 3.2 milliequivalents/gm dry weight), 20 gm, is added to the solution, and the mixture is stirred to keep the resin and sodium sulfate suspended. The solution warms slightly due to the heat of neutralization of $H_2SO_4$; the temperature is maintained between 25° and 30° C. After 5 min., stirring is stopped, and a small portion of the supernatant (about 0.5 ml) is removed and briefly centrifuged to form a Dowex 1 and sodium sulfate free supernatant. Two to 3 drops (about 200 $\mu$l) of the resulting supernatant are then added to about 1 ml of aqueous 2% $BaCl_2$. Formation of a white precipitate indicates that sulfate is still present in the supernatant, and another portion of Dowex 1 resin (5 gm) is added to the reaction mixture. Stirring is continued an additional 5 min. taking care that the sides of the flask are occasionally washed down by swirling the solution by hand. The solution is then again tested for sulfate, and additional 5 gm portions of resin are added at about 5 min. intervals until a sulfate free supernatant is obtained. When no precipitate is formed with $BaCl_2$, a final 5 gm portion of Dowex 1 resin is added to remove unesterified glutathione and traces of sulfate. After stirring 2 to 3 min., the suspension is filtered under vacuum using a medium-porosity fritted glass funnel. The flask and resin are washed with an additional 25 ml of ethanol, and the combined filtrates are immediately transferred to a dry flask, covered to exclude moisture, and kept at $-20°$ C. overnight. Crystallization begins almost immediately.

The resulting fluffy crystals are collected by filtration and washed briefly with cold ethanol and room temperature ethyl ether. Air is drawn through the filter to partially dry the crystals, and they are then transferred to a vacuum desiccator and dried over $P_2O_5$. The yield of the white crystals of glutathione monoethyl ester is 4 gm (about 70%). $C_{12}H_{21}N_3O_6S \cdot \frac{1}{2}H_2O$ (MW=344.4) requires C=41.85%; H=6.44%; N=12.20%. Found: C=42.09%; H=6.37%; N=12.15%. The melting point (uncorrected) is 169°-171° C. High performance liquid chromatography confirmed the structure and showed substantially pure (>99% pure) product. Analysis for total sulfhydryl content using 5,5'-dithio-bis(2-nitrobenzoic acid) indicated 100±2% of theoretical. Aqueous solutions of product are pH 7 and are free of sulfates as indicated by testing with $BaCl_2$.

The above synthesis was repeated several times using 35 to 45 gms of dry Dowex 1 resin (hydroxide form) to obtain substantially equal yields and purity to that obtained above.

When equal volumes of absolute isopropanol are substituted for the ethanol and a reaction time of 50 hours is allowed, yields of 65 to 75% substantially pure neutral glutathione monoisopropyl ester are obtained.

EXAMPLE II

Ethanol, sulfuric acid and glutathione are mixed in the amounts and by the steps set forth in Example I and stirred to obtain a clear solution. To this solution is added 4 gms of 2,2-diethoxypropane. Stirring is continued until unesterified glutathione is less than 3% as indicated by high performance liquid chromatography. To the resulting solution is added 500 ml of ethyl ether whereby glutathione monoethyl ester (sulfate salt) precipitates and is collected and dried. The 2,2-diethoxypropane reacts with water which may be present in reagents or equipment and as it is produced by the esterification reaction, to form acetone and ethanol. Thus, the 2,2-diethoxypropane drives the equilibrium toward esterification including accommodating for water which may be present. In contrast to use of insoluble dehydrating agents, such as sodium sulfate, which must be removed prior to isolation of monoester salt, neither 2,2-diethoxypropane not its hydrolysis products is insoluble and use of it rather than insoluble dehydrating agent eliminates the need for a separation step.

Many variations of inventive embodiments will be obvious to those skilled in the art. Thus, the inventive embodiments are defined by the claims.

What is claimed is:

1. A method for forming neutral glutathione mono $C_{1-10}$ alkyl ester in which the glycine carboxyl is esterified, to form and isolate said ester without the intermediate isolation of the ester acid salt, said method comprising the steps of
    (a) esterifying glutathione with anhydrous $C_{1-10}$ linear or branched alkyl monohydric alcohol in the presence of strong acid catalyst under conditions such that glutathione and its esters remain soluble in the reaction mixture,
    (b) treating said reaction mixture of step (a) with anhydrous base anion exchange resin (basic form) to neutralize the acid, to bind acid anion and to bind unesterified glutathione,
    (c) separating the resulting resin and associated bound materials to leave a neutral clear solution,
    (d) crystallizing said neutral monoester from said neutral clear solution.

2. The method of claim 1 wherein step (a) is carried out in the presence of dehydrating agent to remove water product of esterification to drive the esterification reaction in the direction of ester formation.

3. The method of claim 2 wherein said dehydrating agent is insoluble in said alcohol.

4. The method of claim 3 wherein said dehydrating agent is sodium sulfate.

5. The method of claim 1 wherein in step (a), the alcohol is selected from the group consisting of methanol, ethanol and isopropanol, the acid catalyst is sulfuric acid and the reaction temperature ranges from 0° to 50° C., and in step (b) said resin is a strong base anion exchange resin in the hydroxide form used in a stoichiometric excess of up to about 25% over the amount needed to neutralize the catalyst, and wherein step (d) is carried out at a temperature ranging from 20° C. to $-20°$ C.

6. The method of claim 5 wherein step (a) is carried out in the presence of sodium sulfate dehydrating agent to remove water product of esterification from solution.

7. The method of claim 1 wherein step (b) comprises treating said reaction mixture of step (a) with anhydrous base anion exchange resin in suspension.

* * * * *